(12) United States Patent
Müller et al.

(10) Patent No.: US 6,511,655 B1
(45) Date of Patent: Jan. 28, 2003

(54) COSMETIC OR DERMATOLOGICAL PREPARATIONS OF THE OIL-IN-WATER TYPE

(75) Inventors: Anja Müller, Rümpel (DE); Heinrich Gers-Barlag, Kummerfeld (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/636,780

(22) Filed: Aug. 11, 2000

(30) Foreign Application Priority Data

Aug. 16, 1999 (DE) .......................... 199 38 757

(51) Int. Cl.⁷ .............................. A61K 7/42; A61K 6/00
(52) U.S. Cl. .......................... 424/59; 424/401
(58) Field of Search .................... 424/59, 401

(56) References Cited

U.S. PATENT DOCUMENTS 5,489,431 A * 2/1996 Ascione et al. ............. 424/401
5,788,952 A * 8/1998 Gers-Barlag et al. ......... 424/59

FOREIGN PATENT DOCUMENTS

| DE | 692 02 759 T2 | 10/1995 |
|---|---|---|
| DE | 44 25 268 A1 | 1/1996 |
| DE | 44 29 468 A1 | 2/1996 |
| DE | 195 45 789 A1 | 6/1997 |
| DE | 196 31 219 A1 | 2/1998 |
| DE | 196 33 012 A1 | 2/1998 |
| DE | 196 35 057 A1 | 3/1998 |
| DE | 695 03 933 T2 | 12/1998 |
| DE | 197 35 900 A1 | 2/1999 |
| DE | 697 00 324 T2 | 11/1999 |
| EP | 0 610 926 A1 | 8/1994 |
| EP | 0 683 662 B1 | 11/1995 |
| EP | 0 823 249 A1 | 2/1998 |
| EP | 0 882 445 A1 | 12/1998 |
| EP | 0 895 775 A1 | 2/1999 |
| EP | 0 908 172 A1 | 4/1999 |
| WO | WO 98/42300 | 10/1998 |

* cited by examiner

*Primary Examiner*—Jose' G. Dees
*Assistant Examiner*—Robert DeWitty
(74) *Attorney, Agent, or Firm*—Norris McLaughlin & Marcus

(57) ABSTRACT

Low-viscosity cosmetic or dermatological preparations of the oil-in-water type, which comprise an oil phase, in which hydrophobic and/or amphiphilic solids are incorporated, and a water phase, where the difference in density between the oil phase and the water phase (determinable using a computerized digital density meter of the type DMA 45 from chempro/PA at 25° C.) is not greater than 0.01 g·cm⁻³, and method of stabilizing O/W formulations.

14 Claims, No Drawings

COSMETIC OR DERMATOLOGICAL PREPARATIONS OF THE OIL-IN-WATER TYPE

The present invention relates to cosmetic and dermatological preparations of the oil-in-water type, in particular sprayable O/W emulsions, which have a viscosity of less than 2000 mPa·s, and to a method of stabilizing O/W formulations by matching the density of the phases.

Cosmetic preparations are essentially used for skincare. The human skin is man's largest organ and performs numerous vital functions. Having an average area of about 2 m$^2$ in adults, it has a prominent role as a protective and sensory organ. Amongst its many functions (for example for heat regulation), the barrier function, which prevents the skin (and therefore ultimately the entire organism) from drying out, is by far the most important. At the same time, the skin acts as a protective device against the invasion and the absorption of external substances (e.g. dirt, chemicals, microorganisms). In addition, it has an important role as a regulatory and target organ in human metabolism.

The main aim of cosmetic skincare is to strengthen or rebuild the skin's natural function as a barrier against environmental influences and against the loss of endogenous substances (as well as water, also natural fats, electrolytes etc.).

Another aim of skincare is to compensate for the loss by the skin of lipids and water caused by daily washing. This is particularly important if the natural regeneration ability is inadequate. Furthermore, skincare products should protect against environmental influences, in particular against sun and wind, and delay skin ageing.

The harmful effect of the ultraviolet part of solar radiation on the skin is generally known. Depending on their respective wavelength, the rays have different effects on the skin organ: UV-C radiation having a wavelength of less than 290 nm is absorbed by the ozone layer in the earth's atmosphere and is of no physiological importance. By contrast, rays in the range between 290 nm and 320 nm, the UV-B region, cause erythema, simple sunburn or even burns of varying severity. UV-A radiation (320 to 400 nm) is much more harmful than UV-B radiation with regard to the triggering of photodynamic, specifically phototoxic, reactions and chronic changes in the skin. For example, UV-A radiation on its own under very normal everyday conditions is enough to damage collagen and elastin fibres within a short period. The harmful effect of UV-B radiation can also be further intensified by UV-A radiation.

In addition, even very low radiation dosages can trigger photochemical reactions. These include, in particular, the formation of free radicals, which in turn can trigger uncontrolled secondary reactions as a result of their high reactivity. In order to prevent such reactions, as well as UV filter substances, it is also possible to additionally add antioxidants and/or free-radical scavengers to cosmetic or dermatological formulations.

Medicinal topical compositions usually comprise one or more medicaments in an effective concentration. For the sake of simplicity, in order to clearly distinguish between cosmetic and medicinal use and corresponding products, reference is made to the legal provisions of the Federal Republic of Germany (e.g. Cosmetics Directive, Foods and Drugs Act).

By far the most important type of product in the field of skincare compositions are emulsions. Emulsions are disperse two- or multi-phase systems, cosmetic emulsions consisting of at least one fatty phase (fats and mineral oils, fatty acid esters, fatty alcohols etc.) and at least one water phase (water, glycerol, glycols etc.), which are distributed in the form of very fine droplets in one another using emulsifiers. If the oil phase is finely distributed in the water phase, then this is an oil-in-water emulsion (O/W emulsion, e.g. milk). The basic character of an O/W emulsion is determined by the water, i.e. is less greasy on the skin, is rather matting and absorbs more rapidly into the skin than a W/O emulsion.

Although, when viewed from a thermodynamic viewpoint, emulsions are unstable systems, it is possible to prepare cosmetic emulsions which are stable for years.

An emulsion is described as stable if, over a pregiven period of time, no measurable temporal or spatial changes in the droplet size distribution can be established.

The stability or instability of emulsions depends on a variety of factors. Firstly, the water phase of a W/O emulsion tends, for example, towards sedimentation since the water and oil phases have different densities. The oil phase of an O/W emulsion, accordingly, has a tendency towards creaming.

In addition, because of the forces of attraction between the finely distributed droplets of the disperse phase, drop aggregation can result, where the individual droplets of an aggregate remain initially separate from one another by a thin film of the continuous phase. In this case, the original droplet size distribution only seemingly changes and can in this case be restored by stirring or shaking.

However, the droplets which are in contact can, moreover, also coalesce, which leads to a real change in the droplet size distribution, which can only be changed back by inputting energy. This phenomenon is referred to as coalescence. The more viscous the outer phase of the emulsion, the more slowly the process of coalescence proceeds.

The processes described can occur individually or together. One process often initiates or intensifies the other. Thus, for example, the formation of aggregates in O/W emulsions accelerates creaming of the oil phase. If the disperse state of an emulsion is partially or completely lost, then the two phases separate, and this is referred to as emulsion breaking.

Accordingly, the stabilization of emulsions over a relatively long period of time requires auxiliaries which prevent separation of the two phases, or at least delay it until the emulsion has fulfilled its intended purpose.

These auxiliaries should firstly stabilize the interface by preventing the droplets of the disperse phase from coalescing. In the ideal case, these substances moreover effect repulsion of the droplets, which prevents them from contacting, thus avoiding agglomeration (aggregate formation).

Secondly, auxiliaries are used to counteract creaming or sedimentation of the phases.

Emulsifiers are interface-active substances which are able to prevent the interfacial tension between oil and water phase by positioning themselves preferably at the interface between these two phases. This is made possible as a result of their amphiphilic molecular structure: emulsifiers have at least one polar (hydrophilic) group and at least one nonpolar (lipophilic) group. As a result, they are soluble both in the hydrophilic phase and in the lipophilic phase. The part which is more soluble in the corresponding phase protrudes into this phase and as a result lowers the interfacial tension between the two phases.

The attempt to classify emulsifiers is difficult since they belong to categories which are very different in chemical terms. The more quickly an emulsifier lowers the interfacial tension and the lower the equilibrium value of the interfacial tension, the more effective the emulsifier.

Moreover, emulsifiers also stabilize as a result of the formation of interfacial films and thus "physical" barriers, as a result of which aggregate formation and coalescence of the emulsified particles is prevented. As a result of the positioning of the emulsifier at the interface, the droplets either become charged, so that they mutually repel, or a stable, often high-viscosity or even solid protective layer is formed around the droplets.

However, for the practical preparation of cosmetic or dermatological emulsions, the use of one or more emulsifiers on their own is generally insufficient. Important factors for the stability of cosmetic or dermatological preparations are also:

very fine distribution of the two phases in one another the smaller the dispersed particles, the more stable the emulsion.

high viscosity of the outer phase a stable interfacial film a balanced phase volume ratio The emulsifier system must therefore in most cases comprise, in addition to the actual emulsifier, a further component which is referred to as coemulsifier, stabilizer or, depending on the activity mechanisms, also as bodying agent, thickener or protective colloid etc.

These substances, which for the sake of simplicity are referred to below as stabilizers, increase the stability of an emulsion. Stabilizers must not be surface-active, but can be amphiphilically constructed compounds.

One option of stabilizing emulsions is, in accordance with that stated above, to increase the viscosity of the outer phase. This viscosity increase generally brings about a considerable reduction in the mobility of the dispersed droplets, as a result of which the rate of sedimentation or creaming is reduced. As a result of this, the droplets also meet less frequently, which results in a lower tendency towards coalescence.

The viscosity of the external phase can, for example, be increased by adding thickeners which form, for example, gels and/or lamellar liquid crystals. In principle, emulsifiers are also able to increase the viscosity of a liquid as a result of the formation of emulsifier gel networks. However, this requires a relatively large amount of emulsifier since gel networks are only formed when the total interface between the phases is coated with emulsifier molecules.

The breaking of an emulsion can also be prevented by the choice of a suitable phase volume ratio. To illustrate this fact, imagine an emulsion as a system of metal spheres of equal diameter (internal phase) and a liquid (external phase). Sedimentation or creaming can—in this simple model, no longer occur if the entire liquid is filled with metal spheres. Assuming as dense as possible a sphere packing as distribution, this is the case precisely at a ratio of 1:2, i.e. when ⅔ of the emulsion consists of an internal phase. It is obvious that the viscosity of an emulsion increases as the proportion of internal phase grows since the mobility of the dispersed droplets becomes restricted as a result.

The person skilled in the art is of course aware of the large number of options for formulating stable O/W preparations for cosmetic or dermatological use, for example in the form of creams and ointments, which are spreadable in the range from room to skin temperature, or as lotions and milks, which are flowable in this temperature range. In this connection, as well as the choice of the "right" emulsifier or emulsifier system, the further composition of the preparation, in particular, is important.

O/W emulsions are generally stabilized by thickeners which increase the viscosity of the aqueous phase. Examples of suitable thickeners for this purpose are polyacrylates (carbomers) and other organic thickeners. A disadvantage of this method of improving the stability is the sensitivity of these formulations towards electrolytes. In addition, mainly higher-viscosity formulations (such as creams or ointments) are of course to be prepared in this manner. The stabilization of O/W emulsions above the phase volume ratio also generally leads to viscous formulations.

Emulsions of "liquid" (=flowable) consistency are used in cosmetics, for example as care, cleansing, face or hand lotions. They generally have a viscosity of from about 2000 mPa·s to about 10,000 mPa·s. The stability of flowable emulsions requires particular attention since the considerably greater mobility of the particles encourages more rapid coalescence.

These prior art liquid emulsions—since they too generally comprise thickeners—are not stable towards relatively high concentrations of electrolyte either, which manifests itself in phase separation. It is, however, frequently desirable to use certain electrolytes, such as, for example, water-soluble UV filters, in order to be able to utilize the other physical, chemical or physiological properties thereof. Although in many cases appropriate choice of the emulsifier system can provide remedies to a certain extent, other disadvantages then arise just as often.

The discussed disadvantages can, for example, lie in the fact that relatively large amounts of one or more emulsifiers are required (e.g. 3% by weight or above). Since, however, even emulsifiers—as ultimately any chemical substance— can in individual cases trigger allergic reactions or reactions based on oversensitivity of the user (although the use of customary cosmetic emulsifiers is of course generally entirely acceptable), it is desirable to keep the emulsifier content of a cosmetic or dermatological formulation as low as possible.

Emulsions with a very low viscosity (low-viscosity or sprayable emulsions) have hitherto, in accordance with that stated above, only been able to be formulated with considerable effort, if at all. Accordingly, the supply of such formulations is extremely low. Nevertheless, such formulations could offer the consumer cosmetic results which are hitherto unknown.

European Patent Specification 667 144 describes cosmetic sun protection compositions which are oil-in-water emulsions and comprise inorganic nanopigments based on metal oxides as light protection agents, it also being possible for the formulations to be sprayable. These preparations are PIT emulsions, which are prepared by phase inversion and are therefore particularly finely disperse. However, this specification was unable to point the way to the present invention.

Generally, low-viscosity preparations of the prior art frequently have the disadvantage that they are limited to a narrow area of application or a restricted choice of raw materials. The incorporation of relatively high concentrations of polar oil components also frequently presents problems. It is, however, in some cases desirable to incorporate large amounts of polar oil components into a formulation, for example to dissolved solid UV filter substances and in so doing to be able to achieve a high sun protection factor.

An object of the present invention was to prepare preparations of the oil-in-water type which have a very low viscosity and do not have the disadvantages of the prior art. A further object of the invention was to discover ways of producing cosmetic or dermatological, as low-viscosity as possible, O/W emulsions which are stable towards increased electrolyte concentrations, and into which large amounts of polar oil components can be incorporated. It was also an object of the invention to find a method of stabilizing O/W formulations.

Surprisingly, these objects are achieved by low-viscosity cosmetic or dermatological preparations of the oil-in-water type, which comprise an oil phase, in which hydrophobic and/or amphiphilic solids are incorporated, and a water phase, where the difference in density between the oil phase and the water phase (determinable using a computerized digital density meter of the type DMA 45 from chempro/PA at 25° C.) is not greater than 0.01 g·cm$^{-3}$ and, if desired, comprising customary cosmetic or dermatological auxiliaries, additives and/or active ingredients.

The invention also provides a method of stabilizing O/W formulations, characterized in that the density of the oil phase is matched to the density of the water phase by adding hydrophobic and/or amphiphilic solids in such a way that the difference in density between the two phases is not greater than 0.01 g·cm$^{-3}$.

O/W formulations obtainable by this process are also provided by the present invention.

The preparations according to the invention are entirely satisfactory preparations in every respect and are not limited to a restricted choice of raw materials. Accordingly, they are very particularly suitable for use as bases for preparation forms having diverse application purposes. The preparations according to the invention have excellent stability against decomposition in oil and water phases and exhibit very good sensory properties, such as, for example, spreadability on the skin or ability to be absorbed into the skin.

It was particularly surprising that the preparations according to the invention are extraordinarily stable even without the addition of further stabilizers—such as, for example, bodying agents, thickeners or protective colloids etc.—and that, for example, relatively large amounts of polar oil components can be incorporated without problems.

The preparations according to the invention represent an enrichment of the prior art with regard to low-viscosity O/W emulsions in every respect.

In addition, very stable O/W formulations, for example sprayable formulations with a high light protection factor are obtainable in a surprisingly simple manner by the process according to the invention.

It is particularly advantageous according to the invention if the preparations comprise significantly less than 1% by weight (based on the total weight of the preparations) of one or more emulsifiers. Very particular preference is given to preparations according to the invention which—based on the total weight of the preparations—comprise less than 0.5% by weight of one or more emulsifiers or which are even entirely free from emulsifiers.

It is also advantageous if the average diameter of the oil droplets of the formulations according to the invention is less than 50 μm. Preference is given for the purposes of the present invention to formulations whose overall density is greater than 0.9 g·cm$^{-3}$, in particular greater than 0.95 g·cm$^{-3}$.

It can also be advantageous if the O/W formulations according to the invention, although it is not necessary, also comprise stabilizers, which are advantageously chosen from the group of thickeners. It is advantageous to choose the content of one or more thickeners from the range 0.05% by weight to 0.15% by weight, based on the total weight of the preparations.

Solids

Advantageous amphiphilic solids for the purposes of the present invention, are, for example, modified phyllosilicates.

Silicates are salts and esters (silicic esters) of orthosilicic acid [Si(OH)$_4$] and condensation products thereof. Silicates are not only the class of minerals which contain the most types, but are also extremely important from a geological and industrial viewpoint. Over 80% of the earth's crust consists of silicates. Phyllosilicates are (ideally) silicate structures having two-dimensionally infinite layers of [SiO$_4$]$^{4-}$ tetrahedra, each tetrahedron being bonded to neighbouring tetrahedra by 3 bridging oxygens.

Only approximate chemical formulae can be given for phyllosilicates since they have a large ion-exchange capability, and silicon can be replaced by aluminium, and this in turn can be replaced by magnesium, Fe$^{2+}$, Fe$^{3+}$, Zn and the like. The negative charge of the layers which may result is usually balanced by cations, in particular by Na$^+$ and Ca$^{2+}$ in interlayer positions.

Phyllosilicates can swell by reversible intercollation of water (in a 2- to 7-fold amount) and other substances, such as, for example, alcohols, glycols and the like. Their use as thickeners in cosmetic compositions is, accordingly, known per se. However, the prior art was unable to point the way to the present invention.

Advantageous phyllosilicates for the purposes of the present invention are, for example, those whose greatest expansion direction in the unmodified and unswollen state has, on average, a length of less than 10 μm. For example, the average expansions of the modified phyllosilicate particles used can be 1000 nm×100 nm×1 nm and below. The effective size of the modified phyllosilicate particles in a cosmetic or dermatological formulation naturally depends on the amount of intercollated substances.

Advantageous modified phyllosilicates for the purposes of the present invention are, for example, modified smectites. Smectites are always very finely particulate (in most cases <2 mm) three-layer clay minerals (2:1 phyllosilicates) which occur mainly as lamella-shaped, moss-like or spherical aggregates, in which a central layer of octahedrally coordinated cations is sandwiched by two layers of [(Si,Al)O$_4$] tetrahedra. Smectites are described in an idealized manner by the following structural formula, in which circles filled in white represent silicon and/or aluminium atoms, circles filled in pale grey are oxygen atoms, circles filled in dark grey are hydrogen atoms, and circles filled in black are aluminium, magnesium, iron atoms and/or other exchange cations:

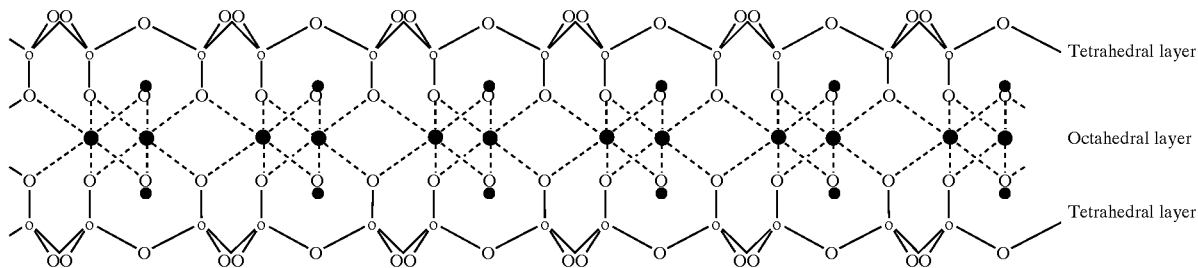
Tetrahedral layer
Octahedral layer
Tetrahedral layer

Advantageous modified smectites are, for example, modified montmorillonites. Montmorillonites are described by the approximated chemical formula $Al_2[(OH)_2/Si_4O_{10}]\cdot nH_2O$ or $Al_2O_3\cdot 4SiO_2\cdot H_2O\cdot nH_2O$, and are clay minerals belonging to the dioctahedral smectites.

Also particularly advantageous for the purposes of the present invention are, for example, modified hectorites. Hectorites belong to the smectites and have the approximate chemical formula $M^+_{0.3}(Mg_{2.7}Li_{0.3})[Si_4O_{10}(OH)_2]$, in which $M^+$ is in most cases $Na^+$.

Also advantageous for the purposes of the present invention are modified bentonites. Bentonites are clays and rocks which contain smectites, especially montmorillonite, as main minerals. The "crude" bentonites are either calcium bentonites (referred to in Great Britain as fuller's earths) or sodium bentonites (also: Wyoming bentonites).

Modified phyllosilicates for the purposes of the present invention are phyllosilicates, in particular the phyllosilicate types already mentioned, whose organophyllicity (also: lipophyllicity) has been increased, for example by reaction with quaternary ammonium compounds. Such phyllosilicates are also referred to as organophyllic phyllosilicates.

Particularly advantageous for the purposes of the present invention are bentones, i.e. organic derivatives of montmorillonites (or bentonites) and/or hectorites, which are prepared by ion-exchange reactions with alkylammonium bases.

Advantageous modified phyllosilicates for the purposes of the present invention are obtainable, for example, by reacting phyllosilicates with quaternium-18. Quaternium-18 is a mixture of quaternary ammonium chloride salts which are described by a defined structural formula:

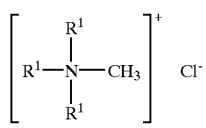

in which the radicals $R^1$ are independently of one another chosen from the group consisting of methyl and hydrogenated tallow radicals having a chain length of from 12 to 20 carbon atoms.

According to the invention, particular preference is given to stearalkonium hectorite, a reaction product of hectorite and stearalkonium chloride (benzyldimethylstearylammonium chloride), and quaternium-18 hectorite, a reaction product of hectorite and quaternium-18, which are available, for example, under the trade names Bentone 27 and Bentone 38 from Nordmann & Rassmann.

Advantageous hydrophobic and/or amphiphilic solids are also X-ray amorphous oxide pigments. X-ray amorphous oxide pigments are metal oxides or semimetal oxides which reveal no or no recognizable crystal structure in X-ray diffraction experiments. Such pigments are often obtainable by flame reaction, for example by reacting a metal or semimetal halide with hydrogen and air (or pure oxygen) in a flame.

Preferred X-ray amorphous oxide pigments are silicon oxides of the Aerosil® type (CAS No. 7631-86-9). Aerosils®, which are obtainable from DEGUSSA AG/Frankfurt are characterized by a small particle size (e.g. between 5 and 40 nm), the particles being regarded as spherical particles of very uniform dimension. Macroscopically, Aerosils® are recognizable as loose, white powders.

Advantageous Aerosil® grades are, for example, Aerosil® OX50, Aerosil® 130, Aerosil® 150, Aerosil® 200, Aerosil® 300, Aerosil® 380, Aerosil® MOX 80, Aerosil® MOX 170, Aerosil® COK 84, Aerosil® R 202, Aerosil® R 805, Aerosil® R 812, Aerosil® R 974, Aerosil® R976.

Further advantageous hydrophobic and/or amphiphilic solids are, for example, micronized, inorganic pigments which are chosen from the group of amphiphilic and/or hydrophobic metal oxides, in particular from the group consisting of titanium oxide, zinc oxide and silicon dioxide, it being possible for the metal oxides to be present either individually or in a mixture. In this connection, it is essentially unimportant in which of the potentially naturally occurring modifications the amphiphilic metal oxides used are present.

It is advantageous to choose the average particle diameter of pigment used to be between 1 nm and 200 nm, particularly advantageously between 5 nm and 100 nm.

According to the invention, the cosmetic and dermatological preparations can also comprise hydrophobic inorganic micropigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

It is also advantageous for the purposes of the present invention to use virtually pure pigment particles, in particular those which can be used as dye in the foods industry. The zinc oxide pigments obtainable from Merck and those obtainable under the trade names Zinkoxid neutral from Haarmann & Reimer or NanoX from Harcros Chemical Group, for example, are advantageous.

For the purposes of the present invention, advantageous virtually pure pigment particles are also the boron nitrides listed below:

| Trade name | Obtainable from |
| --- | --- |
| Boron Nitride Powder | Advanced Ceramics |
| Boron Nitride Powder | Sintec Keramik |
| Ceram Blanche | Kawasaki |
| HCST Boron Nitride | Stark |
| Très BN ® | Carborundum |
| Wacker-Bornitrid BNP | Wacker-Chemie |

It is advantageous to choose the average particle diameter of the boron nitride particles used to be less than 20 μm, particularly advantageously less than 15 μm.

Also advantageous according to the invention are solids which have been surface-treated ("coated") to repel water, the intention being to form or retain a hydrophobic and/or amphiphilic character of these solids. This surface treatment may involve providing the solids with a thin hydrophobic layer by methods known per se.

Such a process, which is described below using titanium dioxide as an example, consists, for example, in producing the hydrophobic surface layer by a reaction in accordance with

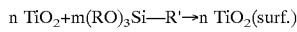

n and m are stoichiometric parameters to be used as desired, and R and R' are the desired organic radicals. $TiO_2$ pigments, for example those coated with aluminium stearate and obtainable under the trade name MT 100 T from TAYCA, are particularly advantageous.

A further advantageous coating consists of aluminium hydroxide or hydrated aluminium oxide (also: Alumina, CAS No.: 1333-84-2), to which stearic acid is then applied. It is moreover also preferred to apply other hydrophobic coatings to metal oxide particles pretreated with alumina, such as, for example, polyorganosiloxanes. Advantageous hydrophobic titanium dioxide pigments coated with alumina and stearic acid are available, for example, under the trade name UV Titan M160 from Kemira.

A further advantageous coating of the solids according to the invention consists of dimethylpolysiloxane (also: dimethicone), a mixture of completely methylated, linear siloxane polymers which are terminally blocked with trimethylsiloxy units. Particularly advantageous for the purposes of the present invention are zinc oxide pigments and boron nitride particles which are coated in this manner. The boron nitride particles treated with dimethicone and available from Carborundum under the trade name Très BN® UHP 1106, for example, are advantageous.

Also advantageous is a coating with polymethylhydrogensiloxane, a linear polysiloxane which is also referred to as methicone. Advantageous boron nitride particles coated with methicone are, for example, those obtainable from Carborundum under the trade name Très BN® UHP 1107.

It is also advantageous if the solids according to the invention are coated with a mixture of dimethylpolysiloxane, in particular dimethylpolysiloxane having an average chain length of from 200 to 350 dimethylsiloxane units, and silicagel, which is also referred to as simethicone. It is particularly advantageous if the inorganic pigments are additionally coated with aluminium hydroxide or hydrated aluminium oxide (also: alumina, CAS No.: 1333-84-2). Titanium dioxides which are coated with simethicone and alumina, where the coating can also comprise water, are particularly advantageous. One example of this is the titanium dioxide obtainable under the trade name Eusolex T2000 from Merck.

Also advantageous according to the invention are, for example, titanium dioxide pigments coated with octylsilanol, and/or the silicon dioxide particles which have been surface-treated to repel water. Preference is given, for example, to spherical polyalkylsilsesquioxane particles, as mentioned in European Laid-Open Specification 0 686 391. Such polyalkylsilsesquioxane particles are available, for example, under the trade names Aerosil R972 and Aerosil 200V from Degussa.

Also advantageous for the purposes of the present invention are mixtures of different inorganic, amphiphilic pigment types both within a crystal, for example as iron mixed oxide or talc (magnesium silicate), and also by mixing two or more types of metal oxide within a preparation. Magnesium silicates are particularly advantageous, for example those available under the trade name Talkum Micron from Grolmann.

Also advantageous according to the invention are dispersions of ultrafine titanium dioxide in oils or oily titanium dioxide suspensions, e.g. titanium dioxide in caprylic/capric triglyceride, a mixture of triglycerides mainly of caprylic acid $[CH_3(CH_2)_6COOH]$ and of capric acid $[CH_3(CH_2)_8COOH]$. Preference is given, for example, to the oily titanium dioxide suspensions available under the trade name Tioveil TG from Solaveil.

Also advantageous for the purposes of the present invention are lustre or pearlescent pigments, in particular also silver and gold lustre pigments. Preference is given to pulverulent pigments or castor oil dispersions of bismuth oxychloride and/or titanium dioxide, and bismuth oxychloride and/or titanium dioxide on mica. Such bismuth oxychlorides are supplied in varying qualities by Merck Rona under the trade name Biron. Biron LF 2000, for example, is advantageous. Particular preference is also given to the pearlescent pigments available under the trade name Mica from Merck KgaA, in particular Mica Black, which is a mixture of iron oxide ($Fe_3O_4$), mica and titanium dioxide, and Mica M.

Advantageous solids for the purposes of the present invention are also pigments which have a colouring action, for example those listed below (in brackets the Colour Index Numbers according to the *Rowe Colour Index, 3rd edition, Society of Dyers and Colourists, Bradford, England,* 1971 and the shade): Pigment Green (10006, green), Pigment Yellow 1 (11680, yellow), Pigment Yellow 3 (11710, yellow), Pigment Orange 1 (11725, orange), Pigment Red 3 (12120, red), Pigment Red 112 (12370, red), Pigment Red 7 (12420, red), Pigment Brown 1 (12480, brown), Pigment Yellow 16 (20040, yellow), Pigment Yellow 13 (21100, yellow), Pigment Yellow 83 (21108, yellow), Pigment Violet 23 (51319, violet), Pigment Red 122 (73915, red), Pigment Blue 16 (74100, blue), Aluminium (77000, white), hydrated alumina (77002, white), Pigment Red 101 and 102 (77015, red), barium sulphate (77120, white), carbon (77266, black), Pigment Black 9 (77267, black), Carbo medicinalis vegetabilis (77268:1, black), Pigment Blue 28 and Pigment Green 14 (77346, green), Pigment Metal 2 (77400, brown), Gold (77480, brown), iron oxides and hydroxides (77489, orange), iron oxide (77491, red), hydrated iron oxide (77492, yellow), iron oxide (77499, black), mixtures of iron(II) and iron(III) hexacyanoferrate (77510, blue), Pigment White 18 (77713, white) and silver (77820, white).

Other advantageous hydrophobic and/or amphiphilic solids are microfine polymer particles which are present in the preparation in the form of solids. Favourable examples for the purposes of the present invention are polycarbonates, polyethers, polyethylene, polypropylene, polyvinyl chloride, polystyrene, polyamides, polyacrylates and the like.

Advantageous examples are microfine polyamide particles, in particular those available under the trade name SP-500 from TORAY. Also advantageous are polyamide 6 (also: nylon 6) and polyamide 12 (also: nylon 12) particles. Polyamide 6 is the polyamide [poly(ε-caprolactam)] built up from ε-aminocaproic acid (6-aminohexanoic acid) or ε-caprolactam, and polyamide 12 is a poly(ε-laurolactam) of ε-laurolactam. Advantageous examples for the purposes of the present invention are Orgasol® 1002 (polyamide 6) and Orgasol® 2002 (polyamide 12) from ELF ATOCHEM.

Further advantageous microfine polymer particles are microfine polymethacrylates. Such particles are available, for example, under the trade name POLYTRAP® from DOW CHEMICAL.

It is particularly advantageous, although not obligatory, for the microfine polymer particles to be surface-coated. This surface treatment can involve providing the polymer particles with a thin hydrophilic layer by methods known per se. Advantageous coatings consist, for example, of titanium dioxide ($TiO_2$), zirconium dioxide ($ZrO_2$) or else of other polymers, such as, for example, polymethyl methacrylate. Particularly advantageous microfine polymer particles for the purposes of the present invention are, for example, those available by the process described in U.S. Pat. Specification No. 4,898,913 for the hydrophilic coating of hydrophobic polymer particles.

The average particle diameter of the microfine polymer particles used is preferably chosen to be less than 100 μm, particularly advantageously less than 50 μm. In this connection, it is essentially unimportant in which form (platelets, rods, spherules etc.) the polymer particles used are present.

Further preferred hydrophobic and/or amphiphilic solids are amphiphilic modified polysaccharides which do not exhibit thickening properties.

Such amphiphilic polysaccharides are, for example, obtainable by reacting starch with mono-, bi- or polyfunctional reagents or oxidizing agents in reactions which proceed in a largely polymer-analogous manner.

These reactions are based essentially on modifications of the hydroxyl groups of the polyglucans by etherification, esterification or selective oxidation. This produces, for example, starch ethers and starch esters of the general structural formula Structural formula I

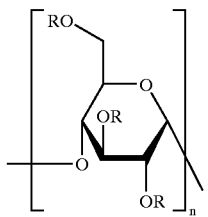

in which R can, for example, be a hydrogen and/or an alkyl and/or aralkyl radical (in the case of starch ethers) or a hydrogen and/or an organic and/or inorganic acid radical (in the case of starch esters). Starch ethers and starch esters are advantageous for the purposes of the present invention.

It is particularly advantageous to use starch ethers, e.g. those which are obtainable by etherification of starch with tetramethylolacetylenediurea and which are referred to as non-mucilaginous starch (nonswelling starch).

Particularly advantageous are starch esters and/or salts thereof, for example sodium and/or aluminium salts of half-esters of starch which have low degrees of substitution, in particular sodium starch n-octenyl succinate of the structural formula I in which R is characterized by the following structure

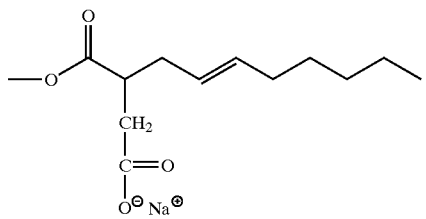

and which is available, for example, under the trade name Amiogum® 23 from CERESTAR, and aluminium starch octenyl succinate, in particular those available under the trade names Dry Flo® Elite LL and Dry Flo® PC from CERESTAR.

Also advantageous is Distarch Phosphate (INCI), which is formed by crosslinking starch with sodium metaphosphate and is available under the trade name Mais OP from chemag.

It is advantageous to choose the average particle diameter of the modified polysaccharides to be less than 20 μm, particularly advantageously less than 15 μm.

The list of given modified polysaccharides which can be combined with the modified phyllosilicates is not of course intended to be limiting. Modified polysaccharides which are advantageous solids for the purposes of the present invention are obtainable in numerous ways, either chemical or physical, which are known per se. For the preparation of such polysaccharides, novel ways are in principle also conceivable. In this connection, it is important that the modified polysaccharides display hydrophobic and/or amphiphilic properties and that they do not have thickening action.

In all of the above cases, it is advantageous to choose the total concentration of all pigments to greater than 0.05% by weight, particularly advantageously between 0.05% by weight and 30% by weight, based on the total weight of the preparations, where the total content of one or more hydrophobic and/or amphiphilic solids is to be chosen such that the difference in density between the oil phase and the water phase (determinable using a computerized digital density meter of the DMA 45 type from chempro/PA at 25° C.) is not greater than 0.01 g·cm$^{-3}$.

The hydrophobic and/or amphiphilic solids are incorporated into the oil phase of the formulations. Depending on the nature of the product in question, the amounts of solids to be used in each case can be readily determined by the person skilled in the art by simple exploratory experiments without inventive activity.

Oil Phase

The oil phase of the O/W emulsions according to the invention is advantageously chosen from the group of polar oils, for example from the group of lecithins and of fatty acid triglycerides, namely the triglycerol esters of saturated and/or unsaturated, branched and/or unbranched alkanecarboxylic acids having a chain length of from 8 to 24, in particular, 12 to 18, carbon atoms. The fatty acid triglycerides can, for example, advantageously be chosen from the group of synthetic, semisynthetic and natural oils, such as, for example, caprylic/capric triglyceride, cocoglyceride, olive oil, sunflower oil, soya bean oil, peanut oil, rapeseed oil, almond oil, palm oil, coconut oil, castor oil, wheatgerm oil, grapeseed oil, thistle oil, evening primrose oil, macadamia nut oil and the like.

For the purposes of the present invention, further advantageous polar oil components can also be chosen from the group of esters of saturated and/or unsaturated, branched and/or unbranched alkanecarboxylic acids having a chain length of from 3 to 30 carbon atoms and saturated and/or unsaturated branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of octyl palmitate, octyl cocoate, octyl isostearate, octyldodecyl myristate, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can advantageously be chosen from the group of dialkyl ethers, dicaprylyl ether, for example, being advantageous.

It is also preferred to choose the oil component(s) from the group consisting of isoeicosane, neopentyl glycol diheptanoate, propylene glycol dicaprylate/dicaprate, caprylic/capric/diglyceryl succinate, butylene glycol caprylate/caprate, $C_{12-13}$-alkyl lactate, di-$C_{12/13}$-alkyl tartrate, triisostearin, dipentaerythrityl hexacaprylate/hexacaprate, propylene glycol monoisostearate, tricaprylin, dimethyl isosorbide. It is particularly advantageous for the oil phase of the O/W emulsions according to the invention to have a content of $C_{12-15}$-alkyl benzoate, or to consist entirely of this.

Any desired mixtures of such oil and wax components are also to be used advantageously for the purposes of the present invention.

In addition, the oil phase of the O/W emulsions according to the invention can likewise advantageously also comprise nonpolar oils, for example those chosen from the group of branched and unbranched hydrocarbons and waxes, in particular mineral oil, vaseline (petrolatum), paraffin oil, squalane and squalene, polyolefins, hydrogenated polyisobutenes and isohexadecane. Of the polyolefins, polydecenes are the preferred substances.

The oil phase can also advantageously have a content of cyclic or linear silicone oils, or consist entirely of such oils, although it is preferred to use an additional content of other oil phase components apart from the silicone oil or the silicone oils.

Cyclomethicone (octamethylcyclotetrasiloxane) is advantageously used as the silicone oil to be used according to the invention. However, other silicone oils can also be used advantageously for the purposes of the present invention, for example cetyldimethicone, hexamethylcyclotrisiloxane, polydimethylsiloxane, poly(methylphenylsiloxane).

Also advantageous according to the invention are, for example, natural waxes of animal and vegetable origin, such as, for example, beeswax, chinese wax, bumble-bee wax and other insect waxes, in particular those mentioned below.

Beeswax, for example, is an excretion product from the glands of honey bees which the latter use to build honeycombs. Yellow (Cera flava), brown or red so-called crude wax is, for example, obtainable by melting the honeycombs freed from honey by centrifugation, separating the melt from solid impurities, and allowing the resulting crude was to solidify. The crude wax can be bleached completely white by treatment with oxidizing agents (Cera alba).

Beexwax consists of cerin, which is readily soluble in alcohol and is a mixture of cerotic acid $CH_3(CH_2)_{24}COOH$ and melissic acid $CH_3(CH_2)_{28}COOH$, and of an ester mixture called myricin consisting of about 70 esters of $C_{16}$- to $C_{36}$-acids and $C_{24}$- to $C_{36}$-alcohols. Essential constituents of beeswax are myricyl palmitate, myricyl cerotinate and paraffin.

Other insect waxes, such as, for example, bumble-bee wax, shellac wax or Chinese wax are essentially mixtures of various esters. Chinese wax, for example, is deposited or produced in China and Japan from the wax scale louse (Coccus ceriferus) living on the Chinese ash and the scale species Ceroplastes ceriferus and Ericerus pela. It is scraped from the trees and purified by remelting in boiling water. The main constituent of Chinese wax is the cerotic ester of ceryl alcohol.

Shellac wax is obtained from lac, the secretion of the female lac insects (Kerria lacca), which live in huge colonies (lac is derived from the Hindi word "Lakh" for 100,000) on trees and shrubs in southern Asia (India, Burma, southern China). The shellac wax obtainable by solvent extraction contains, as essential constituents, myricyl alcohol, melissic acid and other wax alcohols and acids or esters thereof. Plant waxes are also advantageous for the purposes of the present invention.

Those preferably used are cuticular waxes of lower or higher plants, algae, lichens, mosses and fungi, such as, for example, candelilla wax, carnauba wax, Japan wax, esparto grass wax, cork wax, rice wax, sugarcane wax, fruit waxes, e.g. apple wax, flower waxes, leaf waxes from conifers, coffee wax, flax wax, sesame wax, jojoba oil and the like.

Candelilla waxes, for example, are brownish to yellowish brown, hard waxy materials which are soluble in lipophilic solvents. Candelilla wax contains odd-number aliphatic hydrocarbons (about 42%), esters (about 39%), wax acids and wax alcohols. It can be obtained, for example, from the comminuted, fleshy leaves of a thornless spurge species (Euphorbia cerifera) by boiling with aqueous sulphuric acid.

Carnauba wax is a yellowish, greenish or dark-grey material which can be obtained in varying qualities, obtained by selection, from the leaves of the Brazilian fan palm Copernicia prunifera or carnauba palm (*Carnauba cerifera*) by, for example, brushing the wax dust from the withered fronds, melting it and filtering it and, after solidification, breaking it into pieces. Carnauba wax can be lightened by bleaching agents. It contains about 85% of esters, in each case approximately 2–3% of free wax acids (carnaubic, behenic, lignoceric, melissic and cerotic acid), long-chain alcohols, diols and unsaturated hydrocarbons.

Japan wax (also: Japan tallow or Cera japonica) is colourless or yellowish, pure plant fat which can be obtained, for example, in Japan from the fruits of a tree-like sumach plant (Rhus succedanea) by boiling. The main constituents of Japan wax are palmitic glycerol esters and esters of Japanic acid (heneicosanedioic acid, $C_{21}H_{40}O_4$), phellogenic acid (docosanedioic acid, $C_{22}H_{42}O_4$) and of tricosanedioic acid ($C_{23}H_{44}O_4$).

Esparto wax is obtained as a byproduct in the manufacture of pulp and paper from the esparto grass (Graminaceae) indigenous to Mediterranean countries. It consists of about 15 to 17% of wax acids (e.g. cerotic and melissic acid), of 20 to 22% of alcohols and hydrocarbons, and of 63 to 65% of esters.

Particularly advantageous natural waxes for the purposes of the present invention are, for example, those available under the trade name Permulgin 1550 and Permulgin 4002 from KOSTER KEUNEN, and those available under the trade names Schellack Wachs 7302 L and Candellila Wachs 2039 L from KAHL wax refinery.

Also advantageous according to the invention are chemically modified waxes and synthetic waxes. Preferred modified waxes are, for example, beeswax esters, in particular the alkyl beeswaxes available under the trade names BW Ester BW 67, BW Ester BW 80 from KOSTER KEUNEN.

Preferred synthetic waxes are, for example, that available under the trade name beeswax component B 85 from SCHLICKUM, and silicone-based waxes, such as, for example, dialkoxydimethylpolysiloxanes, which are characterized by the following structure

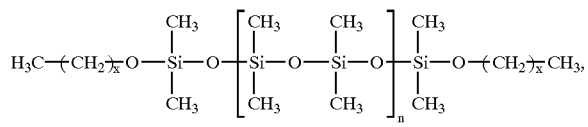

in which x is a number between 18 and 24. Behenoxy dimethicone, for which x from the above structural formula is 21 and which is available under the trade name Abil® Wax 2440 from Th. Goldschmidt AG is particularly advantageous. Also preferred according to the invention is a silicon-based wax available under the trade name Siliconyl Beeswax from KOSTER KEUNEN.

Further advantageous synthetic waxes of certain fatty acids and/or fatty acid mixtures, for example $C_{16-36}$-fatty acids, in particular those available under the trade name Syncrowax AW1C from Croda GmbH.

Also advantageous for the purposes of the present invention are ester waxes, which are esters of
1. a saturated and/or unsaturated, branched and/or unbranched mono- and/or dicarboxylic acid having 12 to 40 carbon atoms and
2. a saturated and/or unsaturated, branched and/or unbranched alcohol having 12 to 40 carbon atoms. Particularly advantageous ester waxes are those chosen from the group listed below:

| Ester wax | Trade name | Available from |
|---|---|---|
| Myristyl myristate | Cetiol MM | Henkel KgaA |
| Cetyl palmitate | Cutina CP | Henkel KgaA |
| $C_{14-34}$ Alkyl stearate | Kesterwachs K 76 H | KOSTER KEUNEN |
| $C_{20-40}$ Dialkyl dimerate | Kesterwachs K 80 D | KOSTER KEUNEN |
| Ditetracosanyl dimerate | Kesterwachs K70D | KOSTER KEUNEN |
| $C_{16-38}$ Alkyl hydroxystearoyl stearate | Kesterwachs K80P | KOSTER KEUNEN |
| $C_{20-40}$ Alkyl stearate | Kesterwachs K 82 | KOSTER KEUNEN |
| Hydroxystearyl hydroxystearate | Elfacos C26 | AKZO NOBEL |

Also advantageous are esters of glycol, in particular glycol esters of lignoceric acid ($CH_3(CH_2)_{22}COOH$), of cerotic acid ($CH_3(CH_2)_{24}COOH$) and/or of montanic acid ($CH_3(CH_2)_{26}COOH$). Very particularly advantageous for the purposes of the present invention are glycol esters of montanic acid ($CH_3(CH_2)_{26}COOH$). An advantageous glycol montanate is, for example, available in a mixture with butylene glycol montanate under the trade name Wax E Pharma from Clariant.

It is also advantageous to choose the wax components from the group of glycerides, in particular from the group of triglycerides. The glycerides and triglycerides listed below are particularly advantageous:

| Glyceride | Trade name | Available from |
|---|---|---|
| $C_{16-18}$-Triglyceride | Cremeol HF-52-SPC | Aarhus Oliefabrik |
| Glyceryl hydroxystearate | Naturchem GMHS | Rahn |
| Hydrogenated coco-glycerides | Softisan 100 | Hüls AG |
| Caprylic/capric/isostearic/adipic triglyceride | Softisan 649 | Dynamit Nobel |
| $C_{18-36}$-Triglyceride | Syncrowax HGLC | Croda GmbH |
| Glyceryl tribehenate | Syncrowax HRC | Croda GmbH |
| Glyceryl tri(12-hydroxystearate) | Thixcin R | Rheox/NRC |
| Hydrogenated castor oil | Cutina HR | Henkel KGaA |
| $C_{16-24}$-Triglyceride | Cremeol HF-62-SPC | Aarhus Oliefabrik |

Also of particular preference for the purposes of the present invention is shea butter, also called karité oil or galam butter (CAS No. 68920-03-6). Shea butter is the fat of seeds or kernels of the plant Butyrospermum Parkii belonging to the family of the Sapotaceae, and consists of approximately 34 to 45% by weight of solid fatty acids (principally stearic acid) and of approximately 50 to 60% by weight of liquid fatty acids (principally comprising oleic acid).

Cosmetic or Dermatological Auxiliaries and Additives

If the O/W formulations according to the present invention are to comprise emulsifiers, then it is advantageous to use those emulsifiers which are suitable for the preparation of O/W emulsions, it being possible for these to be present either individually or else in any combinations with one another.

The emulsifier(s) is/are advantageously chosen from the group consisting of the following compounds: polyglyceryl-2 dipolyhydroxystearate, PEG-30 dipolyhydroxystearate, cetyl-dimethicone copolyol, glycol distearate, glycol dilaurate, diethylene glycol dilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, glyceryl stearate, glyceryl diisostearate, pentaerythrityl monooleate, sorbitan sesquioleate, isostearyl diglyceryl succinate, glyceryl caprate, palm glycerides, cholesterol, lanolin, glyceryl oleate (containing 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20 (Teginacid from Th. Goldschmidt), sorbitan stearate, PEG-7 hydrogenated castor oil, steareth-2, oleth-2, cetyl alcohol and ceteareth-30 (emulsifier E 2209 from Th. Goldschmidt), PEG-5 soya sterol, PEG-6 sorbitan beeswax, ceteth-2, glyceryl stearate SE, methylglucose sesquistearate, PEG-10 hydrogenated castor oil, oleth-3, sorbitan palmitate, PEG-22/dodecyl glycol copolymer, polyglyceryl-2 PEG-4 stearate, laneth-5, ceteth-3, laureth-3, stearyl alcohol and steareth-7 and steareth-10 (emulsifier E-2155 from Th. Goldschmidt), oleth-5, sorbitan laurate, laureth-4, PEG-4 laurate, polysorbate 61, polysorbate 81, beheneth-10, polysorbate 65, polysorbate 80, laneth-10, triceteareth-4 phosphate, triceteareth-4 phosphate and sodium $C_{14-17}$-alkyl sec sulphonate (Hostacerin CG from Hoechst), PEG-8 stearate, glyceryl stearate and PEG-100 stearate (Arlacel 165 from ICI), polysorbate 85, trilaureth-4 phosphate, PEG-25 glyceryl trioleate, oleth-10, steareth-10, ceteth-10, PEG-35 castor oil, sucrose stearate, PEG-8 oleate, trioleth-8 phosphate, PEG-40 sorbitan lanolate, PEG-15 glyceryl ricinoleate, choleth-24 and ceteth-24 (Solulan C-24 from Amerchol), $C_{12-15}$-Pareth-12, PEG-20 glyceryl isostearate, PEG-40 hydrogenated castor oil, PEG-16 soya sterol, PEG-20 glyceryl oleate, PEG-20 stearate, polysorbate 80, PEG-20 methylglucose sesquistearate, PEG-30 glyceryl isostearate, PEG-20 glyceryl laurate, ceteth-20, ceteareth-25, PEG-30 stearate, PEG-30 glyceryl stearate, polysorbate 20, laureth-23, PEG-40 stearate, PEG-30 glyceryl laurate, PEG-50 stearate, PEG-100 stearate, PEG-150 laurate, polyglyceryl-3 methylglucose distearate, ceteareth-12, ceteareth-20 and steareth-21, ceteareth-6, PEG-40 castor oil, sodium cetearyl sulphate, lecithin, laureth-4 phosphate, propylene glycol stearate SE, PEG-25 hydrogenated castor oil, PEG-54 hydrogenated castor oil, glyceryl stearate SE, PEG-6 caprylic/capric glycerides, glyceryl oleate and propylene glycol, PEG-9 stearate, glyceryl lanolate, ceteth-2, polysorbate 60, glyceryl myristate, glyceryl isostearate and polyglyceryl-3 oleate, glyceryl laurate, PEG-40 sorbitan peroleate, laureth-4, glycerol monostearate, ceteareth-3, lanolin acid, isostearyl glyceryl ether, cetearyl alcohol and sodium cetearyl sulphate, steareth-2, PEG-22 dodecyl glycol copolymer, polyglyceryl-2 PEG-4 stearate, pentaerythrityl isostearate, polyglyceryl-3 diisostearate, sorbitan oleate and hydrogenated castor oil and Cera alba and stearic acid, sodium dihydroxycetyl phosphate and isopropyl hydroxycetyl ether, methylglucose sesquistearate, steareth-2 and PEG-8 distearate, steareth-20, isosteareth-20, methylglucose dioleate, sorbitan oleate and PEG-2 hydrogenated castor oil and ozokerite and hydrogenated castor oil, PEG-2 hydrogenated castor oil, PEG-45/dodecyl glycol copolymer, methoxy PEG-22/dodecyl glycol copolymer, hydrogenated cocoglycerides, polyglyceryl-4 isostearate, PEG-40 sorbitan peroleate, PEG-40 sorbitan perisostearate, PEG-20 glyceryl stearate, PEG-8 beeswax, laurylmethicone copolyol, polyglyceryl-2 laurate, stearamidopropyl PG dimonium chloride phosphate, PEG-7 hydrogenated castor oil, triethyl citrate, PEG-20 methylglucose sesquistearate, glyceryl stearate citrate, cetyl phosphate polyglycerol methylglucose distearate, poloxamer 101, potassium cetyl phosphate, isosteareth-10, oleth-20, isoceteth-20, glyceryl isostearate, polyglyceryl-3 diisostearates, cetearyl alcohol and PEG-20 stearate.

The emulsifier(s) is/are particularly preferably chosen from the group of fatty acids which have been completely or partially neutralized with customary alkalines (such as, for example, sodium and potassium hydroxide, sodium and potassium carbonate, and mono- and triethanolamine). Particularly advantageous examples of stearic acid and stearates, isostearic acid and isostearates, palmitic acid and palmitates, and myristic acids and myristates.

According to the invention, the emulsifiers are also preferably chosen from the group of saturated and/or unsaturated, branched and/or unbranched fatty alcohols having 10 to 40 carbon atoms, particular preference being given to butyloctanol, butyldecanol, hexyloctanol, hexyldecanol, octyldodecanol, behenyl alcohol ($C_{22}H_{45}OH$), cetearyl alcohol [a mixture of cetyl alcohol ($C_{16}H_{33}OH$) and stearyl alcohol ($C_{18}H_{37}OH$)], cetyl arachidol [2-hexadecyl-1-eicosanol ($C_{36}H_{73}OH$)], lanolin alcohols (wool wax alcohols which are the non-hydrolysable alcohol fraction of wool wax and obtained after the hydrolysis of wool wax) and/or 2-tetradecyloctadecanol ($C_{32}H_{65}OH$). Advantageous variants of the two last-mentioned fatty alcohols are available under the trade names Isofol 36 and Isofol 32 from Condea.

The list of emulsifiers mentioned which can be used for the purposes of the present invention is not of course intended to be limiting.

The preparations according to the invention can advantageously also comprise one or more hydrocolloids.

Hydrocolloids are macromolecules which have a largely linear structure and have intermolecular forces of interaction, which permit secondary and primary valence bonds between the individual molecules and thus the formation of a reticular structure. Some are water-soluble natural or synthetic polymers which, in aqueous systems, form gels or viscous solutions. They increase the viscosity of the water by either binding water molecules (hydration) or else by absorbing and encapsulating the water into their interwoven macromolecules, at the same time restricting the mobility of the water.

The group of hydrocolloids can be divided as follows into:
  organic, natural compounds, such as, for example, agar agar, carrageen, tragacanth, gum arabic, alginates, pectins, polyoses, guar gum, carob bean flower, starch, dextrins, gelatins, caseine,
  organic, modified natural substances, such as, for example, carboxymethylcellulose and other cellulose ethers, hydroxyethyl- and -propylcellulose and the like,
  organic, completely synthetic compounds, such as, for example, polyacrylic and polymethacrylic compounds, vinyl polymers, polycarboxylic acids, polyethers, polyimines, polyamides,
  inorganic compounds, such as, for example, polysilicic acids, clay minerals, such as montmorillonites, zeolites, silicas.

Examples of hydrocolloids which are preferred according to the invention are methylcelluloses, which is the name for the methyl ethers of cellulose. They are characterized by the following structural formula Structural formula II

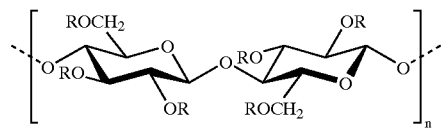

in which R can be a hydrogen or a methyl group.

Particularly advantageous for the purposes of the present invention are the cellulose mixed ethers, which are generally likewise referred to as methylcelluloses, which contain, in addition to a dominating content of methyl groups, also 2-hydroxyethyl, 2-hydroxypropyl or 2-hydroxybutyl groups. Particular preference is given to (hydroxypropyl) methylcelluloses, for example those available under the trade name Methocel E4M from Dow Chemical Comp.

Also advantageous according to the invention is sodium carboxymethylcellulose, the sodium salt of the glycolic ether of cellulose, for which R in structural formula II can be a hydrogen and/or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, which is an anionic heteropolysaccharide which is generally formed by fermentation from maize sugar and is isolated as the potassium salt. It is produced by Xanthomonas campestris and some other species under aerobic conditions with a molecular weight of $2\times10^6$ to $24\times10^6$. Xanthan is formed from a chain having β-1,4-bonded glucose (cellulose) with side chains. The structure of the subgroups ("repeat units") consists of glucose, mannose, glucuronic acid, acetate and pyruvate.

Other hydrocolloids which are advantageous according to the invention are polymers of acrylic acid, in particular those chosen from the group of carbomers or Carbopols (Carbopol® is actually a registered trade mark of the B. F. Goodrich Company). Carbopols are compound of the general structural formula

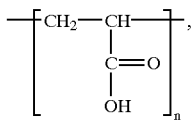

whose molecular weight can be between about 400,000 and more than 4,000,000. The group of Carbopols also includes acrylate-alkyl acrylate copolymers, for example those characterized by the following structure:

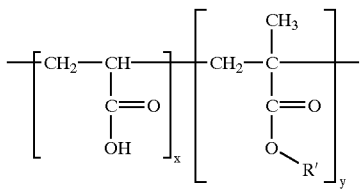

where R' is a long-chain alkyl radical, and x and y are numbers which symbolize the respective stoichiometric content of each comonomer. These Carbopols, too, are also advantageous for the purposes of the present invention.

Examples of advantageous Carbopols are the grades 907, 910, 934, 940, 941, 951, 954, 980, 981, 1342, 1382, 2984 and 5984, it being possible for these compounds to be present individually or in any combinations with one another. Particular preference is given to Carbopol 981, 1382 and 5984 (either individually or in combination with other hydrocolloids).

Also advantageous for the purposes of the present invention are the copolymers, comparable with the acrylate-alkyl acrylate copolymers, of $C_{10-30}$-alkyl acrylates and one or more monomers of acrylic acid, of methacrylic acid or esters thereof. The INCI name for such compounds is "Acrylates/C 10–30 Alkyl Acrylate Crosspolymer". Particularly advantageous are those available under the trade names Pemulen TR1 and Pemulen TR2 from B. F. Goodrich Company.

The total amount of one or more hydrocolloids in the finished cosmetic or dermatological preparations is advantageously chosen to be less than 1.0% by weight, preferably between 0.01 and 0.5% by weight, based on the total weight of the preparations.

The aqueous phase of the preparations according to the invention optionally advantageously comprises alcohols, diols or polyols of low carbon number, and also ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol and glycerol.

Particularly advantageous preparations are also obtained when antioxidants are used as additives or active ingredients. According to the invention, the preparations advantageously comprise one or more antioxidants. Favourable, but nevertheless optional antioxidants to be used are all antioxidants suitable or customary for cosmetic and/or dermatological applications.

The antioxidants are advantageously chosen from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to μmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, the use of oil-soluble antioxidants is particularly advantageous.

A surprising property of the present invention is that preparations according to the invention are good vehicles for cosmetic or dermatological active ingredients into the skin, preferred active ingredients being antioxidants which can protect the skin from oxidative stress. Preferred antioxidants in this connection are vitamin E and derivatives thereof, and vitamin A and derivatives thereof.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant(s), it is advantageous to choose their respective concentrations from the range 0.001 to 10% by weight, based on the total weight of the formulation.

If vitamin A or vitamin A derivatives, or carotenes or derivatives thereof are the antioxidant(s), it is advantageous to choose their respective concentrations from the range 0.001 to 10% by weight, based on the total weight of the formulation.

The person skilled in the art is of course aware that cosmetic preparations are in most cases inconceivable without customary auxiliaries and additives. The cosmetic and dermatological preparations according to the invention can, accordingly, also comprise cosmetic auxiliaries as are customarily used in such preparations, for example bodying agents, fillers, preservatives, perfumes, antifoams, dyes, other surface-active substances, emolients, moisturizers and/or humectants, anti-inflammatory substances, additional active ingredients, such as vitamins or proteins, light protection agents, insect repellents, bactericides, virusides, water, salts, antimicrobial, proteolytic or keratolytic substances, medicaments or other customary constituents of a cosmetic or dermatological formulation, such as alcohols, polyols, polymers, foam stabilizers, organic solvents and also electrolytes.

Corresponding requirements apply mutatis mutandis to the formulation of medicinal preparations.

The O/W emulsions according to the invention can be used as a basis for cosmetic and dermatological formulations. The latter can have the customary composition and be used, for example, for the treatment and care of the skin and/or the hair, as a lipcare product, as a deodorant product and as make-up or make-up remover product in decorative cosmetics or as a light protection preparation. For use, the cosmetic and dermatological preparations according to the invention are applied to the skin and/or hair in a sufficient amount in a manner customary for cosmetics or dermatological compositions.

Accordingly, for the purposes of the present invention, cosmetic or topical dermatological compositions can, depending on their composition, be used, for example, as skin protection cream, cleansing milk, sunscreen lotion, nourishing cream, day or night cream etc. In some instances, it is possible and advantageous to use the compositions according to the invention as bases for pharmaceutical formulations.

The low-viscosity cosmetic or dermatological preparations according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

For the purposes of the present invention, suitable propellants for cosmetic or dermatological preparations which can be sprayed from aerosol containers are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are nontoxic per se which would be suitable in principle for realizing the present invention in the form of aerosol preparations, but which must nevertheless be avoided because of their harmful impact on the environment or other accompanying circumstances, in particular fluorinated hydrocarbons and chlorofluorocarbons (CFCs).

Also favourable are cosmetic and dermatological preparations which are in the form of a sunscreen. These preferably additionally comprise at least one UV-A filter substance and/or at least one UV-B filter substance.

It is, however, also advantageous for the purposes of the present invention to provide cosmetic and dermatological preparations whose main purpose is not protection against sunlight, but which nevertheless have a content of UV protectants. Thus, for example, UV-A or UV-B filter substances are usually incorporated into day creams.

Also, UV protectants, light antioxidants, and if desired, preservatives, provide effective protection of the preparations themselves against decay.

The preparations according to the invention can advantageously comprise substances which absorb UV radiation in the UV-A and UV-B range, the total amount of filter substances being, for example, from 0.1% by weight to 30% by weight, preferably from 0.5 to 20% by weight, in particular from 1.0 to 15% by weight, based on the total weight of the preparations, in order to provide cosmetic preparations which protect the hair and the skin from the whole range of ultraviolet radiation. They can also be used as sunscreens for the hair or the skin.

Advantageous UV-A filter substances for the purposes of the present invention are dibenzoyl methane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Further advantageous UV-A filter substances are phenylene-1,4-bis-(2-benzimidazyl)-3,3'-5,5'-tetrasulphonic acid:

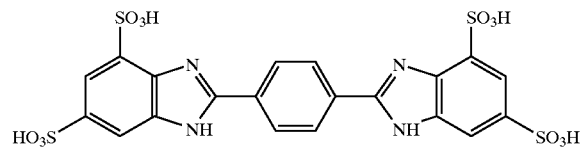

and its salts, particularly the corresponding sodium, potassium or triethanolammonium salts, in particular phenylene-1,4-bis-(2-benzimidazyl)-3,3'-5,5'-tetrasulphonic bis-sodium salt:

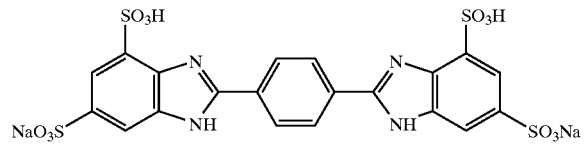

and 1,4-di(2-oxo-10-sulpho-3-bornylidenemethyl)benzene and salts thereof (in particular the corresponding 10-sulphato compounds, in particular the corresponding sodium, potassium or triethanolammonium salt), which is also referred to as benzene-1,4-di(2-oxo-3-bornylidenemethyl-10-sulphonic acid) and is characterized by the following structure:

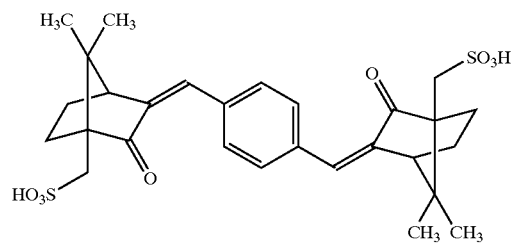

Advantageous UV filter substances for the purposes of the present invention are also broad-band filters, i.e. filter substances which absorb both UV-A and also UV-B radiation.

Advantageous broad-band filters and/or UV-B filter substances are, for example, bisresorcinyltriazine derivates having the following structure:

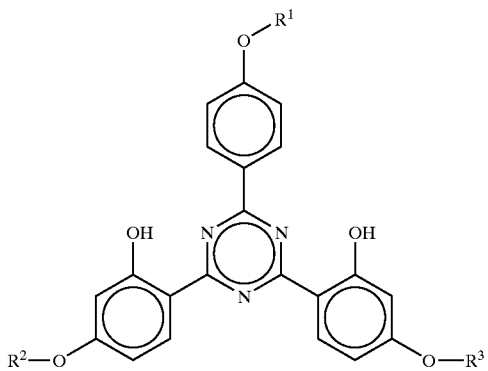

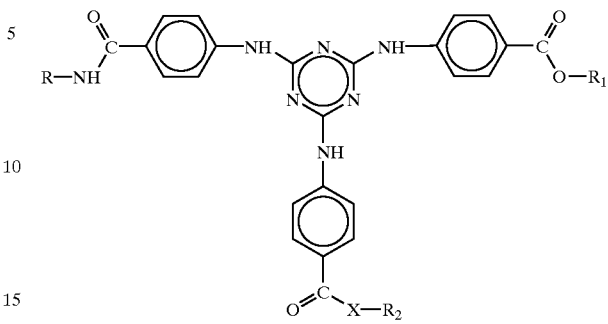

where R¹, R² and R³ independently of one another are chosen from the group of branched and unbranched alkyl groups having 1 to 10 carbon atoms, or are a single hydrogen atom. Particular preference is given to 2,4-bis-{[4-(2-ethylhexyloxy)-2-hydroxy]phenyl}-6-(4-methoxyphenyl)-1,3,5-triazine (INCI: Aniso triazine), which is available under the trade name Tinosorb® S from CIBA-Chemikalien GmbH and to tris(2-ethylhexyl) 4,4',4"-(1,3,5-triazine-2,4,6-triyltriimino)trisbenzoate, synonym: 2,4,6-tris-[anilino-(p-carbo-2'-ethyl-1'-hexyloxy)]-1,3,5-triazine (INCI: Octyl Triazone), which is marketed by BASF Aktiengesellschaft under the trade name UVINUL® T 150.

Other UV filter substances, which have the structural formula

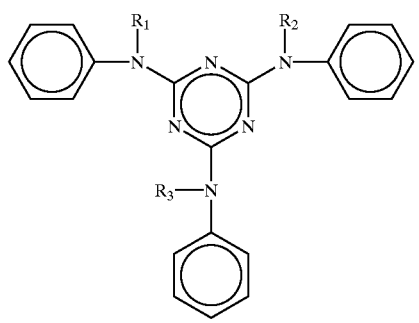

are also advantageous UV filter substances for the purposes of the present invention, for example the s-triazine derivatives described in European Laid-Open Specification EP 570 838 A1, whose chemical structure is expressed by the generic formula where
R is a branched or unbranched $C_1$–$C_{18}$-alkyl radical, a $C_5$–$C_{12}$-cycloalkyl radical, optionally substituted with one or more $C_1$–$C_4$-alkyl groups,
X is an oxygen atom or an NH group,
$R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

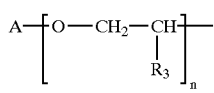

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups,
$R_3$ is a hydrogen atom or a methyl group,
n is a number from 1 to 10,
$R_2$ is a branched or unbranched $C_1$–$C_{18}$-alkyl radical, a $C_5$–$C_{12}$-cycloalkyl radical, optionally substituted by one or more $C_1$–$C_4$-alkyl groups, when X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

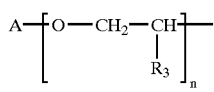

in which
A is a branched or unbranched $C_1$–$C_{18}$-alkyl radical, a $C_5$–$C_{12}$-cycloalkyl or aryl radical, optionally substituted by one or more $C_1$–$C_4$-alkyl groups,
$R_3$ is a hydrogen atom or a methyl group,
n is a number from 1 to 10,
when X is an oxygen atom.
A particularly preferred UV filter substance for the purposes of the present invention is also an unsymmetrically substituted s-triazine, the chemical structure of which is expressed by the formula

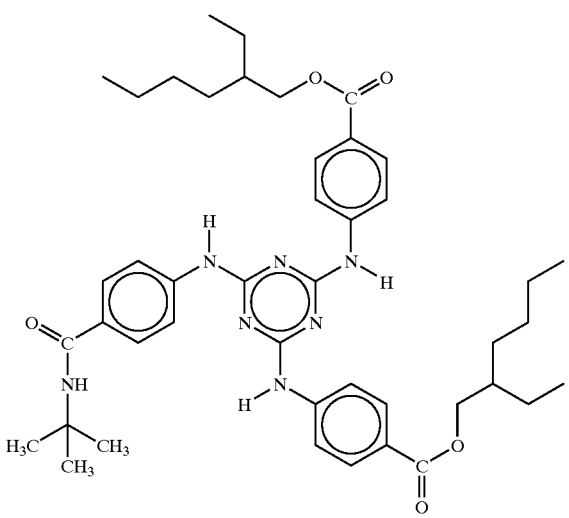

and which is also referred to below as dioctylbutylamidotriazone.

European Laid-Open Specification 775 698 also describes preferred bisresorcinyltriazine derivatives, the chemical structure of which is expressed by the generic formula

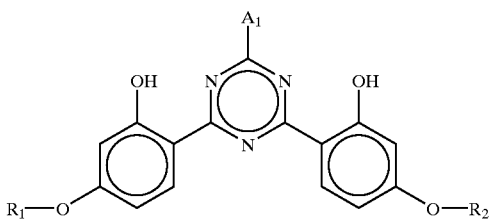

where $R_1$, $R_2$ and $A_1$ represent very different organic radicals.

Also advantageous for the purposes of the present invention are 2,4-bis{[4-(3-sulphonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)-4-(1,1,3,3-tetramethylbutyl)phenol), which is characterized by the chemical structural formula

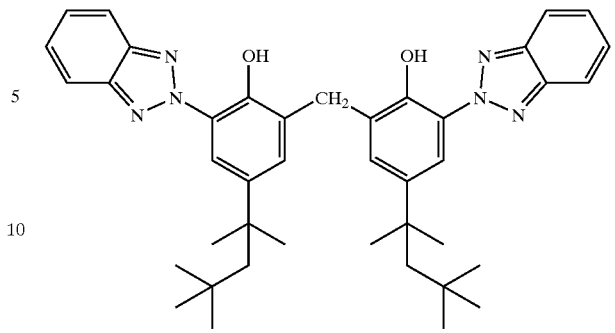

and is available under the trade name Tinosorb® M from CIBA-Chemikalien GmbH.

Another advantageous broad-band filter for the purposes of the present invention is 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) having the INCI name Drometrizole Trisiloxane, which is characterized by the chemical structural formula

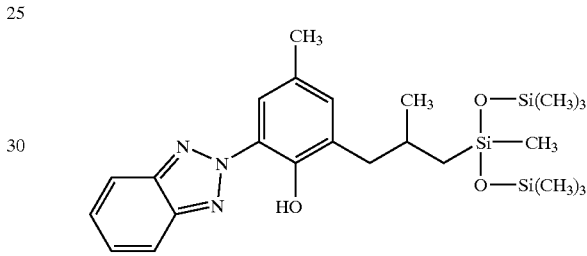

The UV-B filters can be oil-soluble or water-soluble. Examples of advantageous oil-soluble UV-B filter substances are:
- 3-benzylidenecamphor derivatives, preferably 3-(4-methylbenzylidene)camphor, 3-benzylidenecamphor;
- 4-aminobenzoic acid derivatives, preferably 2-ethylhexyl 4-(dimethylamino)benzoate, amyl 4-(dimethylamino)benzoate;
- 2,4,6-trianilino(p-carbo-2'-ethyl-1'-hexyloxy)-1,3,5-triazine;
- esters of benzalmalonic acid, preferably di(2-ethylhexyl) 4-methoxybenzylmalonate,
- esters of cinnamic acid, preferably 2-ethylhexyl 4-methoxycinnamate, isopentyl 4-methoxycinnamate;
- derivates of benzophenone, preferably 2-hydroxy4-methoxybenzophenone, 2-hydroxy4-methoxy-4'-methylbenzophenone, 2,2'-dihydroxy-4-methoxybenzophenone
- and UV filters bonded to polymers.

Examples of advantageous water-soluble UV-B filter substances are:
- salts of 2-phenylbenzimidazole-5-sulphonic acid, such as its sodium, potassium or its triethanolammonium salt, and also the sulphonic acid itself;
- sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)sulphonic acid and salts thereof.

A further light protection filter substance which can be used advantageously according to the invention is ethylhexyl 2-cyano-3,3-diphenylacrylate (octocrylene), which is available from BASF under the name Uvinul® N 539 and is characterized by the following structure:

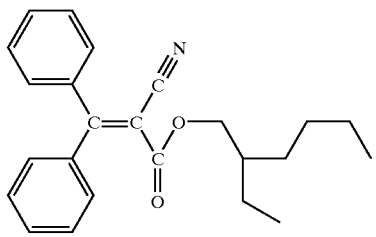

It can also be of considerable advantage to use polymer-bonded or polymeric UV filter substances in the preparations according to the present invention, in particular those described in WO-A-92/20690.

In some instances, it can also be advantageous to incorporate further UV-A and/or UV-B filters in accordance with the invention into cosmetic or dermatological preparations, for example certain salicylic acid derivatives, such as 4-isopropylbenzyl salicylate, 2-ethylhexyl salicylate (=octyl salicylate), homomenthyl salicylate.

The list of given UV filters which can be used for the purposes of the present invention is not of course intended to be limiting.

The examples below serve to illustrate the present invention without limiting it. The numerical values in the examples are percentages by weight, based on the total weight of the respective preparations.

EXAMPLES

|  | 1 | 2 | 3 | 4 | 5 |
|---|---|---|---|---|---|
| Stearic acid | 0.3 |  |  |  |  |
| Cetyldimethicone copolyol |  |  |  | 0.1 |  |
| Glyceryl stearate citrate |  |  |  | 0.5 | 0.3 |
| Dimethicone | 2 | 2.5 |  | 2 |  |
| Phenyltrimethicone | 2 |  | 3 |  |  |
| Caprylic/capric triglyceride | 5 | 5 |  | 5 | 5 |
| $C_{12-15}$-Alkyl-benzoate |  | 5 | 5 | 5 |  |
| Dicaprylyl ether | 5 | 5 | 5 |  | 5 |
| Butylene glycol dicaprylate/caprate |  |  | 5 |  | 2 |
| Mineral oil | 4 |  |  |  |  |
| Cetyl palmitate |  |  |  |  | 0.5 |
| Vitamin E acetate | 0.5 |  | 0.5 |  | 0.5 |
| Dioctylbutamido-triazone |  |  | 1 |  |  |
| Anisotriazine |  |  |  | 2 |  |
| Octyl methoxy-cinnamate |  |  |  | 8 |  |
| Octyltriazone |  | 1 |  |  |  |
| Methylbenzyli-denecamphor |  | 2 |  |  |  |
| Butylmethoxydi-benzoylmethane |  | 1 |  |  |  |
| Eusolex T2000 ® | 2.8 | 2.0 | 2.0 |  |  |
| Aerosil 380 ® |  | 0.6 | 0.6 | 0.4 |  |
| Zinc oxide |  |  |  | 2.5 |  |
| Distarch phosphate |  |  |  |  | 8.5 |
| Preservative | 0.5 | 0.5 | 0.5 | 0.5 | 0.5 |
| Glycerol | 3 | 6 | 10 | 6 | 10 |

-continued

|  | 1 | 2 | 3 | 4 | 5 |
|---|---|---|---|---|---|
| Xanthan gum |  |  |  | 0.1 | 0.1 |
| Pemulen TR1 ® |  |  | 0.1 |  |  |
| Phenylbenzi-midazole-sulphonic acid |  |  | 2 |  |  |
| Sodium hydroxide solution 45% |  |  | 1.2 |  |  |
| Water | ad 100 | ad 100 | ad 100 | ad 100 | ad 100 |

What is claimed is:

1. Low-viscosity cosmetic or dermatological oil-in-water preparations, which comprise an oil phase, in which hydrophobic and/or amphiphilic solids are incorporated, and a water phase, where the difference in density between the oil phase and the water phase (determinable using a DMA 45 computerized digital density meter from chempro/PA at 25° C.) is not greater than 0.01 g·cm$^{-3}$.

2. Preparation according to claim 1, characterized in that further cosmetic or pharmaceutical auxiliaries, additives and/or active ingredients are additionally present.

3. Preparation according to claim 1, characterized in that the viscosity of the preparation is less than 2000 mPa·s (determinable using a Hakke viscometer VT-02 at 25° C.).

4. Preparation according to claim 1 characterized in that the preparation is sprayable.

5. Preparation according to claim 1, characterized in that the diameter of the oil droplets is on average less than 50 μm.

6. Preparation according to claim 1, characterized in that the density of the overall formulation is greater than 0.9 g·cm$^{-3}$.

7. Preparation according to claim 1, characterized in that the content of one or more emulsifiers is less than 1% by weight based on the total weight of the preparation.

8. Preparation according to claim 1, characterized in that it is emulsifier-free.

9. Preparation according to claim 1, characterized in that the content of one or more thickeners is between 0.05% by weight and 0.15% by weight, based on the total weight of the formulation.

10. Method of stabilizing O/W formulations, characterized in that the density of the oil phase is matched to the density of the water phase by adding hydrophobic and/or amphiphilic solids in such a way that the difference in density between the two phases (determinable using a computerized digital density meter of the type DMA 45 from chempro/PA at 25° C.) is not greater than 0.01 g·cm$^{-3}$.

11. A method of protecting skin from the damaging effects of light, said method comprising applying to skin an effective amount therefor of a cosmetic or dermatological preparation according to claim 1.

12. The preparation of claim 3 wherein the viscosity of the preparation is less than 2000 mPa·s.

13. The preparation of claim 6 wherein the density of the overall formulation is greater than 0.95 g·cm$^{-3}$.

14. The preparation of claim 7 wherein the content of one or more emulsifiers is less than 0.5% by weight based on the total weight of the preparation.

* * * * *